(12) United States Patent
Phillips

(10) Patent No.: US 6,733,444 B2
(45) Date of Patent: May 11, 2004

(54) SIDE LOADING SURGICAL RETRACTOR

(76) Inventor: Burns P. Phillips, 1838 Elm Hill Pike, Suite 19, Nashville, TN (US) 37201

( * ) Notice: Subject to any disclaimer, the term of this patent is extended or adjusted under 35 U.S.C. 154(b) by 140 days.

(21) Appl. No.: 10/117,929

(22) Filed: Apr. 5, 2002

(65) Prior Publication Data

US 2003/0191370 A1 Oct. 9, 2003

(51) Int. Cl.[7] ............................................. A61B 17/00
(52) U.S. Cl. ...................................................... 600/213
(58) Field of Search ................................. 600/201, 210, 600/213, 214, 215, 216, 217, 219; 606/54, 59, 61, 62, 64; 403/9, 49, 80, 110, 252, 324, 325, 327, 328; 24/374, 461, 523, 524

(56) References Cited

U.S. PATENT DOCUMENTS

| | | | | | |
|---|---|---|---|---|---|
| 479,146 A | * | 7/1892 | Bradley | ...................... | 278/70 |
| 505,281 A | * | 9/1893 | Smith | ...................... | 24/600.7 |
| 838,767 A | * | 12/1906 | Williams | ...................... | 278/75 |
| 2,845,307 A | * | 7/1958 | Holmes | ...................... | 403/49 |
| 3,227,496 A | * | 1/1966 | Johnson | ...................... | 403/325 |
| 4,544,324 A | * | 10/1985 | Hornung | ...................... | 414/785 |
| 5,297,321 A | * | 3/1994 | Murai | ...................... | 24/600.4 |
| 5,931,777 A | * | 8/1999 | Sava | ...................... | 600/213 |
| 6,042,540 A | * | 3/2000 | Johnston et al. | ............ | 600/213 |
| 6,206,826 B1 | * | 3/2001 | Mathews et al. | ........... | 600/210 |
| 6,305,868 B1 | * | 10/2001 | Kinoshita et al. | ............. | 403/49 |
| 6,324,732 B1 | * | 12/2001 | Arisaka et al. | ............... | 24/458 |
| 6,524,310 B1 | * | 2/2003 | Lombardo et al. | ............ | 606/61 |

* cited by examiner

Primary Examiner—Eduardo C. Robert
Assistant Examiner—David Comstock
(74) Attorney, Agent, or Firm—Stephen J. Stark; Miller & Martin PLLC

(57) ABSTRACT

A surgical retractor includes a side loading socket configured to receive a connector head. A linearly moveable slide retains the connector head within the socket cavity. The slide has a convex face outwardly from the socket cavity which assists in "snapping" in a connector head. A convex inner face assists in retaining an inserted connector head. A notch in the tip of the slide assists in preventing rotation of a connector head having opposing locking pins when one of the pins is received in a recess at the back of the socket cavity. A grip is connected to the slide which may move the slide from a locked to a released position within a slot in the socket body.

16 Claims, 2 Drawing Sheets

US 6,733,444 B2

SIDE LOADING SURGICAL RETRACTOR

FIELD OF THE INVENTION

The present invention relates generally to a surgical retractor apparatus used with interchangeable retractor blades. More particular the present invention relates to a surgical retractor with side loading interchangeable retractor blades.

BACKGROUND OF THE INVENTION

When conducting some surgical procedures, it is often desirable to retract tissue. Although there are a number of procedures and devices available to retract tissue, U.S. Pat. No. 6,042,540 allows for the top loading as well as the side loading of retractor blades into a socket. The side loading feature of this, and other prior art, is believed to be advantageous whereby the surgeon's vision is not obscured while connecting, or disconnecting a blade from a retractor. The '540 patent discloses a number of retractors which can utilize the blade of FIG. 1A, specifically, the longitudinal retractor of FIG. 3, the transverse retractor of FIG. 4, and the side-loading hand-held retractor of FIG. 5. As shown in FIGS. 1A and 1C, the blades typically have connector heads locking pins typically extend from opposite sides of the longitudinal axis of the connector head. Although the '540 patent specifically shows a top loading connector head, other connector heads also employ the opposing locking pin construction.

The '540 patent utilizes a "cam member" to restrain a connector head within a socket cavity. There are believed to be a number of problems with this design. First, cams are known in the art typically as: "a disc or cylinder having an irregular form such that its motion, usually rotary gives to a part or parts in contact with it a specific rocking or reciprocating motion or motions". In the '540 patent, the rotation of the cam 130 about pivot 128 locks and unlocks the connector head from within the socket chamber. One of the perceived drawbacks of this "cam" design is the release lever 124 rotates and extends away from the socket 12 as the cam is moved in and out of the socket chamber.

Another perceived problem with the design shown and described in the '540 patent is the cam is described as being positioned at least partially "within" a side loading socket. While this design appears to allow for the grip of the socket to tighten if a blade were to be attempted to be pulled side-ways out of the socket cavity, this tightening effect also would appear to cause an inserted connector head to bind instead of rotate within the socket cavity.

Accordingly, a need exists for an improved retractor design.

SUMMARY OF THE INVENTION

A need exists for a surgical retractor which accepts blades having a connector head at least in a side loading manner.

Another need exists for a surgical retractor which securely retains connector heads in a socket.

Another need exists for a side loading surgical retractor socket which does not rely on an awkward cam mechanism.

Yet another need exists for a side loading surgical retractor socket which allows a connector head to "snap" in to a locked configuration without a need for an operator to manually operate a locking mechanism.

Accordingly, a surgical retractor includes a body having a socket for receiving a connector head. The socket has a slide which moves linearly toward and away from a connector head when positioned within the socket. A convex surface on a first face of the slide allows for the connector head to be pushed into position or "snapped" in, while a convex surface on a second face of the slide is believed to assist in retaining an inserted connector head in position within the socket. The second face of the socket may also be constructed with a notch at a tip of the slide which allows pinned hubs to be received within the notch to resist turning in at least one direction. While the preferred embodiments accepts only side loaded connector heads, other non-preferred embodiments could accept top loaded connector heads as well.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
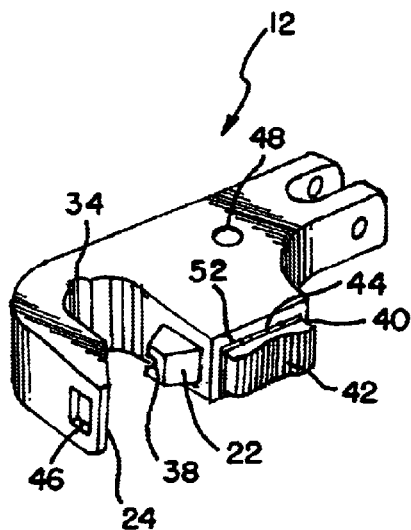
FIG. 1 is a top view of a side-loading retractor with the socket of FIG. 2.

FIG. 1 illustrates a preferred embodiment of a surgical retractor 10 having at least one, and preferably two, sockets 12 as shown in FIGS. 2–5. Other retractor designs may also utilize the socket 12 of the present invention. The socket 12 of this design receives a connector head 14 in a side loading manner. In fact, at least one protuberance, such as one or more pins 16, prevent a connector head 14 from being top loaded in the preferred embodiment as the pins 16 extend into the socket chamber 18. In alternative embodiments, top loading may be allowed, such as if the pins 16 are not provided, do not sufficiently extend within the socket chamber 18, or otherwise. The connector head shown and described in co-pending and co-owned Patent Application No. 60/327,437 works well with the socket 12 of the preferred embodiment.

Figure 2:
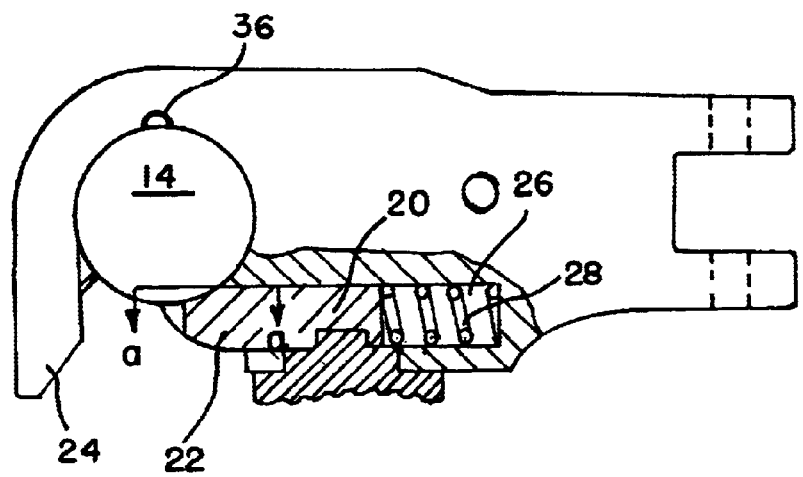
FIG. 2 shows a top perspective view of a surgical retractor socket of the present invention.
Figure 3:
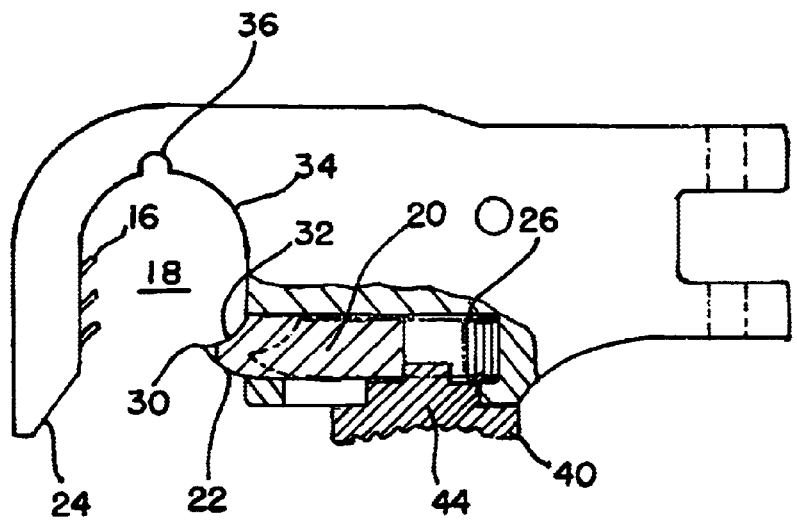
FIG. 3 is a top plan view of the surgical retractor of FIG. 2 with a connector head in place and with some portions illustrated in phantom.
Figure 4:
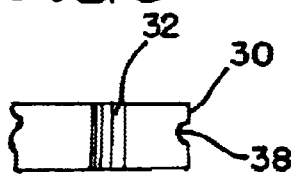
FIG. 4 is a top plan view of the surgical retractor of FIG. 2 with the slide in a partially retracted position.

Instead of using a rotating cam as shown and described in the '540 patent to secure a connector head within the socket chamber as shown in FIG. 2, the preferred embodiment utilizes a linearly moving slide 20. The slide 20 is moveable in a linear manner between a locked position as shown in FIG. 3, and an unlocked position shown in phantom in FIG. 4. FIG. 4 also shows an intermediate position, such as might occur if a connector head 14 were "snapped" into position within the socket chamber 18 as will be described in further detail below.

The slide 20 has a first face 22 which is directed outward from the socket cavity 18. The first face 22 is preferably convex so that when a connector head, which is traditionally cylindrical in shape, is pushed against the first face 22 and director 24 toward the socket cavity 18, the slide 20 is deflected into slot 26. The slot 26 receives the slide 20 so that the slide 20 or other component does not extend further away from the socket 12 to potentially snag something.

Spring 28 normally biases the slide 20 into the locked position shown in FIG. 2. Accordingly, when the bias of spring 28 is overcome by a connector head 14 being directed within the socket cavity 18, the connector head 14 "snaps" into position since once the head clears the tip 30 of the slide 20, it encounters second face 32 which is concave. The concave shape of the second face 32 is believed to be advantageous as it may allow for the circular shape of the socket cavity 18 to be continued so that a circle inscribed along the socket walls 34 would continue along the second face 32. Furthermore the concave shape of the second face 32, in the preferred embodiment, prevents the second face 32 from being positioned in the socket cavity 18.

In the preferred embodiment, the slide 20 has been specifically designed so that it cannot even be partially positioned within the socket 12, as has been done in the prior art. The slide 20 is positioned external to the socket to retain a connector head 14 within the socket cavity 18. In fact the slide 20 may assist in defining the socket cavity 18, especially when the second face 32 of the slide 20 has a similar arc of curvature as the socket wall 34. In other embodiments, the slide 20 may extend into the socket cavity 18.

Adjacent to the socket cavity 18 is a recess 36 which may accept a fixing pin of a connector head. Furthermore, at the tip 30 and/or the first face 32 a notch 38 is located which accepts a second fixing pin of a connector head at least partially therein to assist in prevent the locking pin from rotating toward the slide 20. The illustrated notch 38 prevents the connector head 14 from rotating toward the slide 20 when locking pins, if utilized, are oriented toward the recess 36 and notch 38.

While the connector head 14 maybe snapped into the socket cavity 18 as explained above, the slide 20 may be operated with the grip 40 which preferably has a textured surface 42 for ease of operation. The grip 40 may also be curved to accommodate a user's thumb or finger. The grip is connected to the slide 20 by arm 44. Movement of the grip 40 moves the slide 20 accordingly. The grip 40 is moveable along the socket 12, not away from the socket 12. The slide 20 is linearly moveable within the slot 26.

In order to assist in the construction of slot 26, a cutout 46 in the director 24 allows for the through machining of the slot 26. Additionally, a suture hole 48 may be provided in the socket body 50. As shown in FIG. 1, a groove 52 along a top portion of the body 50 allows the arm 44 to access the slot 26. A similar groove may be located along the bottom portion of the body 50 with another arm.

Figure 5:
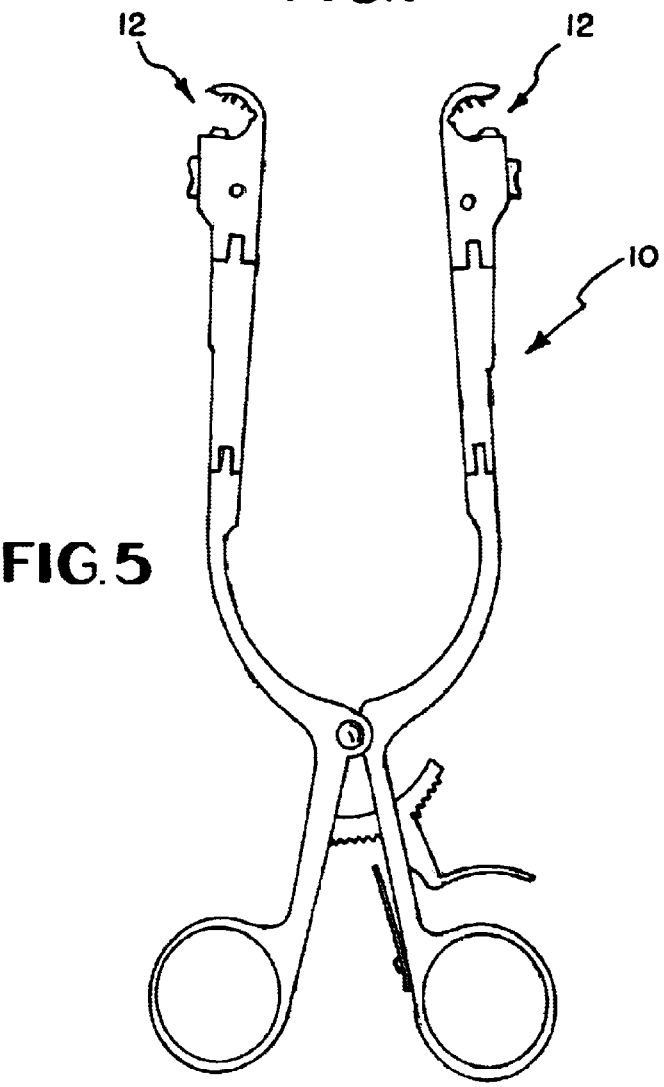
FIG. 5 is a side plan view of the slide taken along the line a—a of FIG. 3.

It is anticipated that surgical retractors 10 such as the type shown in FIG. 5 will utilize the socket of FIGS. 1–4. Other retractor types including longitudinal retractors such as the one shown in FIG. 4 of the '540 patent, and others, may also employ the socket design of the present invention.

While many aspects differentiate the preferred embodiment from the design shown and described in the '540 patent, many aspects of this disclosure could be advantageous incorporated into that design as well to eliminate many Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A surgical retractor further comprising:
a retractor body having a side loading socket cavity for receiving a connector head;
a linearly displaceable slide configured to selectively retain and release a connector head within and from the socket cavity in a locking and a released position; and
at least one protuberance into the socket cavity preventing top loading of the connector head.

2. The surgical retractor of claim 1 wherein the slide has a first face outwardly oriented relative to the socket cavity having a convex surface.

3. The surgical retractor of claim 1 wherein the slide is spring biased in the locking position.

4. The surgical retractor of claim 1 further comprising a grip connected to the slide.

5. The surgical retractor of claim 1 wherein linear movement of the grip moves the slide linearly.

6. The surgical retractor of claim 1 further comprising a director, said director located substantially opposite the slide across the opening into the socket cavity.

7. The surgical retractor of claim 1 having a first face inwardly oriented relative to the socket cavity having a concave surface.

8. The surgical retractor of claim 7 wherein the socket cavity is at least partially bounded by socket walls and the first face has a similar arc of curvature as the socket walls.

9. The surgical retractor of claim 1 further comprising a longitudinal recess at a back of the socket cavity.

10. The surgical retractor of claim 1 wherein the slide operates along an operation axis perpendicular to a longitudinal axis through the connector head.

11. The surgical retractor of claim 10 where the operator axis of the slide does not intersect the longitudinal axis of the connector head.

12. A surgical retractor comprising:
a retractor body having a side loading socket cavity for receiving a connector head;
a linearly displaceable slide configured to selectively retain and release a connector head within and from the socket cavity in a locking and a released position; and
a tip at end of the slide, and a notch at the tip, said notch configured to at least partially receive a locking pin of the connector head.

13. A surgical retractor comprising:
a retractor body having a side loading socket cavity for receiving a connector head;
a longitudinal recess a back of the socket cavity;
a linearly displaceable slide configured to selectively retain and release a connector head within and from the socket cavity in a locking and a released position; and
a notch at a tip of the slide, said notch substantially opposite from the longitudinal recess in the locking position.

14. The surgical retractor of claim 13 wherein the slide retains and releases the connector head from sideways entry and removal.

15. A surgical retractor comprising:
a socket body having a side loading socket cavity for receiving a connector head;
a slot within and surrounded by the socket body except at a slot opening into the socket along an operation axis and a groove communicating the socket with an external portion of the socket body, said groove spaced from the socket opening by a portion of the socket body; and a linearly displacable slide connected to an arm and configured to move at least partially within the slot in a locking and a release position to selectively retain and release a connector head within the socket cavity, said slide moved by the arm extending through the groove into the slot.

16. The surgical retractor of claim 15 wherein the slide has a convex first face outwardly directed from the socket cavity and a concave second face inwardly directed to the socket cavity.

* * * * *